(12) United States Patent
Zakoshansky et al.

(10) Patent No.: US 8,674,145 B2
(45) Date of Patent: Mar. 18, 2014

(54) METHOD FOR ACCELERATION OF CUMENE OXIDATION

(75) Inventors: Vladimir Zakoshansky, Long Grove, IL (US); Andrey Budarev, St. Petersburg (RU)

(73) Assignee: Illa International, L.L.C., Reno, NV (US)

( * ) Notice: Subject to any disclaimer, the term of this patent is extended or adjusted under 35 U.S.C. 154(b) by 357 days.

(21) Appl. No.: 12/165,259

(22) Filed: Jun. 30, 2008

(65) Prior Publication Data
US 2009/0171126 A1 Jul. 2, 2009

Related U.S. Application Data

(63) Continuation-in-part of application No. 11/934,032, filed on Nov. 1, 2007, now Pat. No. 7,393,984.

(60) Provisional application No. 60/984,703, filed on Nov. 1, 2007.

(51) Int. Cl.
*C07C 409/10* (2006.01)

(52) U.S. Cl.
CPC .................................. *C07C 409/10* (2013.01)
USPC .......................................... 568/569; 568/573

(58) Field of Classification Search
CPC ..................................................... C07C 409/10
USPC ................................................ 568/569, 573
See application file for complete search history.

(56) References Cited

U.S. PATENT DOCUMENTS

| | | | |
|---|---|---|---|
| 4,454,077 A * | 6/1984 | Litz ................................. 261/91 |
| 4,900,480 A * | 2/1990 | Litz et al. ...................... 261/36.1 |
| 5,767,322 A | 6/1998 | Zakoshansky et al. |
| 5,908,962 A * | 6/1999 | Zakoshansky et al. ........ 568/571 |
| 6,375,921 B1 * | 4/2002 | Eickhoff et al. ............... 423/588 |
| 6,956,136 B2 | 10/2005 | Dyckman et al. |
| 7,393,984 B1 | 7/2008 | Zakoshansky |
| 2004/0236152 A1 * | 11/2004 | Black et al. .................... 568/414 |
| 2006/0047142 A1 * | 3/2006 | Wonders et al. ............... 562/414 |

FOREIGN PATENT DOCUMENTS

SU 1455596 7/1987

OTHER PUBLICATIONS

Camarasa et al. "A Complete Model for Oxidation Air-lift reactors", Computers and Chemical Engineering, (2001) vol. 25, pp. 577-584.
International Search Report for the International Searching Authority for International Application No. PCT/US2009/049329; International Filing Date: Feb. 17, 2010; 3 Pages.
Written Opinion of the International Searching Authority for International Application No. PCT/US2009/049329; International Filing Date: Feb. 17, 2010; 4 Pages.
Zakoshansky, "An Analysis of Process Technologies and of the Kinetics and the Mechanisms of Corresponding Major Reactions"; Phenol and Acetone; (2009), pp. 93-97.
Guet et al.; "Fluid Mechanical Aspects of the Gas-Lift Technique"; Annu. Rev. Fluid Mech.; 38; pp. 225-249; 2006.
Kruzhalov et al.; "Joint Phenol and Acetone Production"; State Scientific and Technical Publishing House of Chemical Literature; pp. 108-112; 2006; English Translation.

\* cited by examiner

*Primary Examiner* — Rosalynd Keys
(74) *Attorney, Agent, or Firm* — Cantor Colburn LLP

(57) ABSTRACT

The purpose of the present invention is to provide an advantageous method for accelerating the cumene oxidation reaction without the drawbacks of the above-described previously known approaches by utilizing one or more airlift-type tray installed in one or more conventional commercial reactors utilized during the cumene oxidation process. Such a method is of great use in process configurations where it is desirable to achieve a controlled acceleration of the cumene oxidation process without decreasing process selectivity.

7 Claims, 2 Drawing Sheets

METHOD FOR ACCELERATION OF CUMENE OXIDATION

CROSS REFERENCE TO RELATED APPLICATION

The present application claims priority from the commonly assigned provisional patent application entitled "METHOD FOR ACCELERATION OF CUMENE OXIDATION", Ser. No. 60/984,703, filed on Nov. 1, 2007, and further claims priority from the commonly assigned co-pending U.S. patent application, entitled "METHOD FOR PRODUCTION OF CUMENE HYDROPEROXIDE", Ser. No. 11/934,032, also filed on Nov. 1, 2007, which is hereby incorporated by reference in its entirety, and referred to below as the "MPCH Application".

FIELD OF THE INVENTION

This invention relates to the field of the commercial manufacture of petrochemical synthesis products, and in particular, to a method of accelerating the cumene oxidation reaction during the production of cumene hydroperoxide to further decompose it into phenol and acetone.

BACKGROUND OF THE INVENTION

Cumene hydroperoxide (hereinafter "CHP") is commonly produced using one or more well known methods of oxidation of cumene with air oxygen at a high temperature, i.e., oxidation takes place in liquid-gas system. Typically, cumene is oxidized until CHP concentration reaches 20-35 wt. %, because further increase in cumene conversion leads to a significant build-up of by-products resulting in a proportionally lower process selectivity. The oxidation products are then delivered to a vacuum stripping stage where un-reacted cumene is distilled. The stripping bottom product containing about 60-93 weight percent of CHP is then delivered to a CHP cleavage stage, where CHP decomposes into acetone and phenol under influence of an acidic catalyst. It is well known that in conventional oxidation processes, the main CHP formation reaction is accompanied by a number of side reactions.

The effect of side reactions on the main CHP formation reaction depends, among other factors, on process conditions such as one or more of the following: temperature, product residence time in the reactors, and cumene conversion degree. Typically, the main by-products formed in the side reactions are dimehtylbenzene alcohol (hereinafter "DMBA"), acetophenone (hereinafter "AP") and organic acids, such as formic acid, acetic acid, and/or benzoic acid. Formic and benzoic acids serve to catalyze the acidic decomposition of CHP to form phenol and acetone.

The presence of phenol in the reaction products, under the conditions of a radical oxidation process, is extremely undesirable because it results in a dramatic inhibition of the CHP formation reaction and has a significant negative impact on the overall process selectivity. Other inhibitors of CHP formation reaction (such as sulfur-containing trace contaminants, etc.), that may be present as a result of utilization of lower-grade cumene, also have a considerable negative effect on the process.

In fact, research has demonstrated that when employing conventional previously known process technologies, (i.e. without special treatment of the cumene oxidation products with ammonia), the rate of oxidation of low-quality cumene (in which sulfur-containing trace contaminants are present) is so slow that such conventional technologies could scarcely be considered acceptable for commercial processes. Moreover, when the CHP concentration reaches about 20 wt. %, the conversion of cumene starts to decrease, which leads to complete termination of the reaction. The undesirably low rate of reaction at the initial period is a result of the presence of inhibitors that are contained in the cumene, (most commonly, sulfur-containing contaminants). Specifically, the reason for the inevitable slow-down of the oxidation rate over a course of time, is the joint influence on the reaction of inhibitors accumulated in the reactor due to the oxidation reaction itself, as well as inhibitors introduced with fresh cumene. In fact, the rate of formation of radicals in the reactor turns out to be slower than the rate of the radical chain propagation, which leads to the suppression of the process.

The above-incorporated MPCH Application describes a number of previously known attempts to solve the above-described problem. One specific previously known approach to combating the very strong influence of inhibitors present in conventional commercial processes employing low-quality cumene, involves simultaneous use of the following techniques: (1) adding a sufficiently large amount of caustic to the reactor in which the reaction is taking place, and (2) elevating the temperature in the process reactor(s). However, this attempt to deal with the undesirable impurities has the extremely high price of low selectivity of cumene conversion to CHP (85-89 mol. %), and also a low value of cumene conversion (16-18%). As a result, technical CHP produced in the above-described manner, contains 7-9 wt. % of DMBA and 1.6-2.0 wt. % of AP, by-products which predetermine an extremely low selectivity of the cumene oxidation process and phenol process on the whole.

The above-incorporated MPCH Application provides an excellent solution to the problem of dealing with oxidation reaction inhibitors present in cumene to greatly improve process selectivity. Specifically, the MPCH Application disclosed a continuous method of cumene oxidation in a gas-liquid system, where the liquid phase is represented by cumene and its oxidation products and the gas phase is represented by air. The oxidation process can be carried out either in a reactor series or in a single reactor at least one of which is preferably equipped with at least two airlift-type trays. When specific CHP concentration is achieved, the oxidation products are discharged from the reaction zone and treated in a mixing device with aqueous ammonia or water to remove organic acids such as formic acid, benzoic acid, etc. and to remove phenol, which is an inhibitor of oxidation reaction. The cumene oxidation product stream, free of organic acids and phenol, is recycled to the same reactor in the case of single reactor, or is passed to the next reactor of the series in the case of reactor series. In all cases, the oxidation products treated with water or aqueous ammonia are first directed to a unit for separation of aqueous phase from organic products and then anhydrous organic product stream is forwarded to the next reactor of the series, or recycled to the single reactor for the continued cumene oxidation until the required CHP concentration is achieved.

The purpose of the present invention is to provide an advantageous method for accelerating the cumene oxidation reaction without the drawbacks of the above-described previously known approaches. Such a method is of great use in technologies as disclosed in the MPCH Application, as well as in other processes and process configurations where it is desirable to achieve a controlled acceleration of the cumene oxidation process without decreasing process selectivity, and without jeopardizing process safety.

BRIEF DESCRIPTION OF THE DRAWINGS

In the drawings, wherein like reference characters denote corresponding or similar elements throughout the figure.

DETAILED DESCRIPTION OF PREFERRED EMBODIMENTS

The present invention is aimed at eliminating the disadvantages of previously known techniques of accelerating the cumene oxidation reaction during CHP oxidation processes without decreasing process selectivity, and without jeopardizing process safety.

The above-incorporated MPCH Application teaches that continuous withdrawal from the process reactor of reaction inhibiting contaminants (such as sulfur-containing trace elements) introduced to the reactor with cumene, and withdrawal, and reduction in formation, of inhibitors formed in course of the process, dramatically improve process selectivity and safety. This solution has been effective in that it:
  eliminated the inhibiting effect to a great extent and allowed reduction of the process temperature without losing the cumene conversion;
  reached the required productivity of the reactor; and
  simultaneously achieved the selectivity of about 95 mol. % (See Table 1, below), which is equitable with the selectivity value obtained using petrochemical cumene (that is almost free of sulfur-containing trace contaminants).

Figure 1:
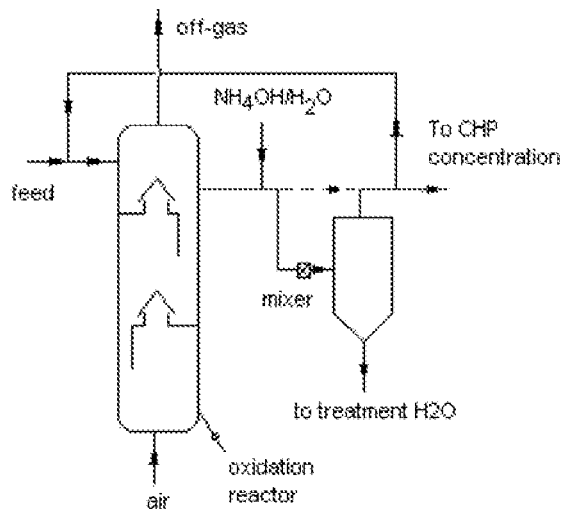
FIG. 1 is a schematic diagram of an implementation of the first embodiment of the inventive method for accelerating the cumene oxidation reaction in a process of producing cumene hydroperoxide in which the oxidation products are treated to remove reaction inhibitors before being returned, and in which a single reactor with plural air-lift trays is shown.

The results discussed above were obtained by Applicants at a continuous pilot unit, which in full scope (except for dimensions) simulated the commercial process, including the arrangement and relevant treatment of all recycle flows. The research, as described below, clearly shows how the pathway of inhibitor control is determined. Referring to FIG. 1 an implementation of the first embodiment of the inventive method for accelerating the cumene oxidation reaction in a process of producing cumene hydroperoxide in which the oxidation products are treated to remove reaction inhibitors before being returned, and in which a single reactor with plural air-lift type trays is shown—this novel approach is utilized as one of the inventive embodiments of the MPCH Application.

Figure 2:
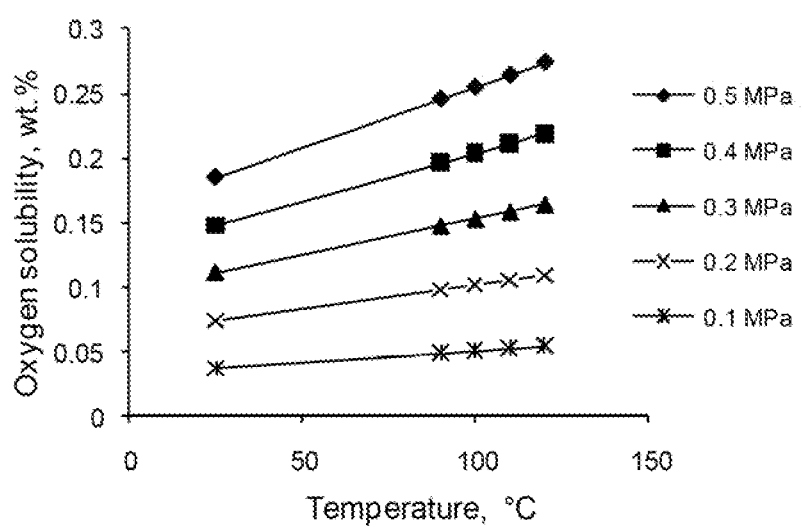
FIG. 2 is a graph showing oxygen solubility in cumene plotted against temperature in an exemplary implementation of the inventive method.

It should be noted that contrary to oxygen present in air bubbles, oxygen dissolved in the liquid phase (FIG. 2) can act as a 'severe' oxidizer, leading to the formation of by-products. Therefore, one may expect that lower concentration of oxygen dissolved in the liquid phase predetermines a higher value of cumene oxidation selectivity.

The oxidizers used in a cumene oxidation process may be complete mixing reactors as proved by the composition of the products taken from the top and bottom of the oxidizer (See Table 1).

TABLE 1

Composition of Oxidizer Overheads/Bottoms, wt. %

| Components | Bottoms | Overheads |
|---|---|---|
| CHP | 19.60 | 19.94 |
| DMBA | 0.91 | 0.88 |
| AP | 0.15 | 0.14 |
| DCP | 0.05 | 0.06 |
| Cumene * | 79.29 | 78.98 |

* estimated as the balance

In reactors operated under complete mixing conditions, composition of the reaction mixture at any point inside the reactor is well-known to be equal to the product composition at the outlet. This is correct for oxygen dissolved in oxidation products to the same degree as for all other specified components. Despite the sufficiently intensive longitudinal mixing of the liquid and gas phases in the oxidizers, the plug-flow conditions are most likely to be created for a part of the rising air bubbles, with a gradual decrease in the oxygen concentration of the air bubbles in the course of their rise from the bottom to the top.

Figure 3:
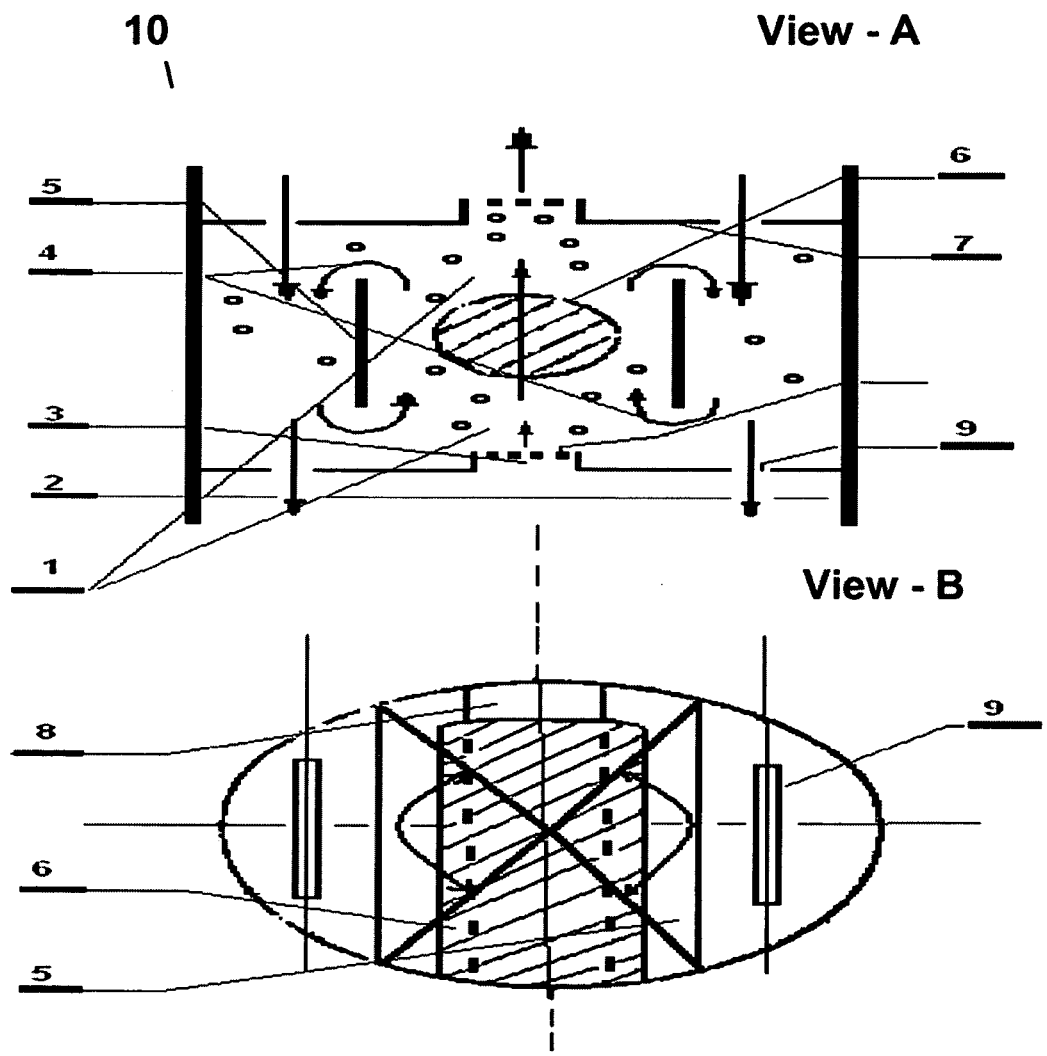
FIG. 3 is a schematic diagram of a second embodiment of the present invention, in which the inventive method involves use of a dedicated oxidizer reactor with at least one airlift-type tray to accelerate the cumene oxidation reaction therein in accordance with the present invention.

Therefore, the statement that the oxygen concentration in the bottom and the middle of the oxidizer is equal to that in the exiting off-gas is scarcely correct. The Applicants' research showed that, when one or more air-lift type trays (as shown in FIG. 3) were installed across the height of oxidizers in a conventional commercial unit, the reaction rate was very noticeably accelerated. To sustain the productivity at the previous level, it was useful to reduce the temperature in all cascade oxidizers by about 5° C.

The reduction in temperature led to a notable growth in selectivity. If the oxygen concentration of the air bubbles in the bottom and middle of the commercial oxidizers had been identical and equal to that in the top, i.e. in the off-gas, then the dispersion of air bubbles on the air-lift trays, regardless of efficiency, would not have sped up the cumene oxidation rate. Replacement of several air-lift trays with a specific airlift-type oxidizer (e.g., such as an oxidizer 10 shown in FIG. 3), made the entire oxidizer work as one air-lift tray and, hence, the oxygen concentration in the air bubbles became equal in the top and bottom. In fact, a forced transition of air bubbles oxygen from plug-flow conditions into less efficient complete mixing conditions takes place in air-lift type oxidizers. At equal volumes of a mixing reactor and a plug-flow reactor, the conversion in a mixing reactor is commonly known to be 20-40% relative lower than that in plug-flow oxidizer (depending on the reaction order).

Referring now to FIG. 3, an exemplary embodiment of a basic design and flow routes in a "gas-lift cell" oxidizer 10, supplied with a plurality of airlift-type trays in accordance with the present invention is shown in a side view A and also in a top-down view B. In view A, the flow routes are shown as ascending gas flow (1), countercurrent liquid flow (2), and circulating flow of reaction mixture (4). A gas blanket (2), and an airlift-type tray (7) are also shown in view A. A vertical baffle (5), heat exchanger (6), and a cut for liquid overflow (9) are shown in both views A and B, while perforated projection (8) in tray (7) for gas bubbling is shown in view B only.

A similar pattern is observed in cumene oxidation in air-lift type oxidizers: the driving force of the reaction decreases due to equalization of the oxygen concentration across the height of the oxidizer, resulting in a slower cumene oxidation rate in the air-lift oxidizers as compared to those equipped with several air-lift trays installed at some distance from each other across the height of oxidizer.

The essence of the present invention is that installation of one or more air-lift trays in a conventional oxidizer/reactor makes maintenance of a desirable oxygen concentration gradient possible in the rising air bubbles between the lower tray and, if present, one or more upper trays, with a diminishment in the size of air bubbles. This is accomplished by positioning at least one airlift-type tray in the bottom portion of the reactor, and, preferably positioning at least one airlift-type tray above (and preferably above a center of the vertical axis of the reactor), such that when the process is conducted, the lower airlift-type tray fractures air bubbles that are formed in the vicinity thereof, and that impact the tray. It should be noted that the specific airlift-type trays shown in FIGS. 1 and 3, are shown by way of example only and are not meant to limit the scope of the invention in any manner. It is contemplated that airlift-type trays of different types, physical constructions, and/or configurations may be readily used without departing from the spirit of the invention, as long as such airlift-type trays possess the features set forth in the description of airlift-type tray functionality in the descriptions accompanying FIGS. 1 to 3 hereto.

Fracturing of the air bubbles by each airlift-type tray may be facilitated by configuring one or more airlift-type trays with perforations on at least a portion of the surface thereof, and/or with other surface deformations that increase the likelihood of an air bubble fracturing into multiple smaller bubbles upon contacting the airlift-type tray.

The continually fractured bubbles are beneficial because they are smaller in size and thus of greater numbers that conventional air bubbles, creating a much larger oxygen contact area of a more uniform dispersal profile for reacting with the organic phase, then unfractured air bubbles, especially when the fractured bubbles rise from the at least one lower airlift-type tray, to the at least one higher airlift-type tray, such that the cumene oxidation reaction occurs at the expanded and more evenly dispersed air bubble—liquid interface. Furthermore, the smaller size of the fractured air bubbles means that they rise slower through the reactor, thus increasing their residence time in the reactor and the duration of their contact with the organic phase.

All these facts combined together allow accelerating the cumene oxidation rate, which, in turn, decreases the temperature and, therefore, boosts the selectivity of the commercial process, and improves its safety.

It is of particular interest to note that the combination of the Ammoxidation technologies with continuous withdrawal of part of the oxidation product from the reactors, followed by treatment of the withdrawn stream by aqueous ammonia solution and recycle of the organic portion of the stream to the reactor has proved that it is possible to solve the problem of employing cumene produced on the basis of coking benzene. The selectivity value of 94.5 mol. % achieved using low-quality cumene containing 2-2.5 ppm of sulfur-containing products (calculated on the basis of sulfur) is a unique phenomenon. The comparison of oxidation results for the above-mentioned low-quality cumene when using conventional technology and the technology developed in the present invention and in the MPCH Application is presented in Table 2, below. The advantages of the inventive technologies over previously known approaches can be readily seen—e.g., the required value of cumene conversion and the required productivity of the reactor utilizing the inventive method are reached at a lower temperature (the average temperature is 101° C.). Most importantly, the selectivity value for oxidation of low-quality cumene to CHP is 7.4% abs. higher than that in the conventional technology, and the selectivity is comparable to the level reached when oxidizing petrochemical cumene.

TABLE 2

Comparison of Oxidation of Cumene with 2.5 ppm of Sulfur-Containing Contaminants: Previously Known (Conventional) Process vs. Inventive Process in accordance with the Method of the Present Invention

| Performance | Technology | |
|---|---|---|
| | Previously Known (Conventional) | Method of the Present Invention |
| Average temp. over cascade, ° C. | 102 (*) 125 | 100 |
| CHP, wt. % | 24.2 | 24.13 |
| DMBA, wt. % | 2.4 | 0.957 |
| AP, wt. % | 0.5 | 0.121 |
| DCP, wt. % | 0.12 | 0.064 |
| Conversion, % | 20.4 | 20.1 |
| Selectivity, mol. % | 87.5 | 94.9 |

(*) - inhibition is so strong that cumene oxidation at first slows down significantly, and then, despite the high concentration of CHP in the reactor, comes to a halt. This inhibition can only be overcome by increasing the temperature up to 125° C., which leads to a significant decrease in the selectivity value.

The acceleration of the cumene oxidation reaction rate due to the installation of at least one airlift-type tray in the oxidizer constitutes evidence that the cumene oxidation reaction occurs at the fractured air bubble—liquid interface. In accordance with the present invention, airlift-type trays provide air bubbles of smaller size and their greater quantity in liquid phase, resulting in a larger and more uniformly dispersed, surface for contact of oxygen-containing bubbles with liquid phase (cumene), which means improvement in oxygen mass transfer from gas phase to liquid phase, and which also have a longer reactor residence time.

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. A method for accelerating a cumene oxidation reaction during a process for producing cumene hydroperoxide (CHP) through cumene oxidation by air oxygen in at least one sequential plug-flow reactor, comprising the steps of:

(a) providing at least one bottom airlift-type tray, operable to fracture and down-size air bubbles that come into contact therewith, wherein said at least one bottom airlift-type tray is positioned entirely in a bottom portion of said at least one sequential plug-flow reactor, such that said at least one sequential plug-flow reactor comprises said at least one bottom airlift-tray in said bottom portion thereof and an air-free area;

(b) generating a "gas-lift" stream comprising cumene and air in said at least one sequential plug-flow reactor to bring said "gas-lift" stream in contact with said at least one airlift-type tray;

(c) fracturing and down-sizing air bubbles of said "gas-lift" stream to ensure mixing and contact between cumene and air and to transfer air bubbles energy of of said "gas-lift" stream at an inlet and outlet of said at least one bottom airlift-type tray to prevent agglomeration of said air bubbles into bubbles of a larger size and to maximize an area of said contact between said cumene and air in said at least one sequential plug-flow reactor; and (d) conducting the cumene oxidation reaction in one of said at least one sequential plug-flow reactor to produce CHP while maintaining a predetermined oxygen and CHP concentration gradient in said at least one sequential plug-flow reactor, such that said gradient extends longitudinally from said bottom plug-flow reactor portion to said top portion thereof, thereby accelerating said oxidation reaction, while decreasing a temperature thereof, boosting process selectivity, and improving process safety.

2. The method for accelerating a cumene oxidation reaction of claim 1, wherein said step (a) further comprises the step of:

(e) providing at least one top airlift-type tray, wherein said at least one top airlift-type tray is positioned entirely in said top portion of said at least one plug-flow sequential reactor, operable to further fracture and downsize said fractured air bubbles coming into contact therewith, wherein said further fractured air bubbles rise above said at least one top airlift-type tray, resulting in a further change in said oxygen concentration between said bottom and top portions of said at least one plug-flow reactor in accordance with said predetermined oxygen concentration gradient.

3. The method for accelerating a cumene oxidation reaction of claim 2, wherein said step (d), further comprises the step of:

(f) continually withdrawing a stream comprising at least a portion of said produced CHP from said at least one plug-flow reactor;

(g) treating said withdrawn stream comprising at least a portion of said produced CHP with an aqueous ammonia solution to form an organic portion and an aqueous portion of said stream;

(h) separating said organic portion of said treated stream; and (i) recycling said organic portion of said treated stream to said at least one sequential plug-flow reactor.

4. The method for accelerating a cumene oxidation reaction of claim 2, wherein said step (e) further comprises the step of:

(j) providing at least one additional airlift-type tray, wherein said at least one additional airlift-type tray is positioned entirely between said top and bottom portions of said at least one plug-flow sequential reactor, operable to further fracture and downsize said fractured air bubbles coming into contact therewith, wherein said further fractured air bubbles rise above said at least one additional airlift-type tray, resulting in a further change in said oxygen concentration between said bottom and top portions of said at least one plug-flow reactor in accordance with said predetermined oxygen concentration gradient.

5. The method for accelerating a cumene oxidation reaction of claim 1, wherein said at least one sequential plug-flow reactor comprises a "gas-lift cell" oxidizer.

6. The method for accelerating a cumene oxidation reaction of claim 1, wherein a selectivity of formation of CHP is 94.9 mole %.

7. The method for accelerating a cumene oxidation reaction of claim 1, wherein an average temperature of said sequential plug-flow reactors is about 101° C.

* * * * *